US009138432B2

(12) United States Patent
Wolfgang et al.

(10) Patent No.: US 9,138,432 B2
(45) Date of Patent: Sep. 22, 2015

(54) METHODS FOR THE ADMINISTRATION OF ILOPERIDONE

(71) Applicant: Vanda Pharmaceuticals, Inc., Washington, DC (US)

(72) Inventors: Curt Wolfgang, Germantown, MD (US); Mihael Polymeropoulos, Potomac, MD (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 0 days.

(21) Appl. No.: 14/150,575

(22) Filed: Jan. 8, 2014

(65) Prior Publication Data

US 2014/0128433 A1 May 8, 2014

Related U.S. Application Data

(63) Continuation of application No. 14/060,978, filed on Oct. 23, 2013, which is a continuation of application No. 11/576,178, filed as application No. PCT/US2005/035526 on Sep. 30, 2005, now Pat. No. 8,586,610.

(60) Provisional application No. 60/614,798, filed on Sep. 30, 2004.

(51) Int. Cl.
*A61K 31/454* (2006.01)
*A61K 31/519* (2006.01)
*C12Q 1/68* (2006.01)

(52) U.S. Cl.
CPC ............. *A61K 31/454* (2013.01); *A61K 31/519* (2013.01); *C12Q 1/6883* (2013.01); *C12Q 2600/106* (2013.01); *C12Q 2600/156* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 4,965,188 A | 10/1990 | Mullis et al. | |
| 5,130,238 A | 7/1992 | Malek et al. | |
| 5,364,866 A | 11/1994 | Strupczewski et al. | |
| 5,846,717 A | 12/1998 | Brow et al. | |
| 5,981,174 A | 11/1999 | Wolf et al. | |
| 6,001,567 A | 12/1999 | Brow et al. | |
| 8,586,610 B2 | 11/2013 | Wolfgang et al. | |
| 2001/0034023 A1 | 10/2001 | Stanton, Jr. et al. | |
| 2002/0022054 A1 | 2/2002 | Sawada et al. | |
| 2002/0127561 A1 | 9/2002 | Bee et al. | |
| 2003/0083485 A1 | 5/2003 | Milos et al. | |
| 2003/0091645 A1 | 5/2003 | Ahlheim et al. | |
| 2003/0144220 A1 | 7/2003 | Obach | |
| 2003/0170176 A1 | 9/2003 | Leyland-Jones | |
| 2004/0072235 A1 | 4/2004 | Dawson | |
| 2004/0091909 A1 | 5/2004 | Huang | |
| 2004/0096874 A1 | 5/2004 | Neville et al. | |
| 2004/0133352 A1 | 7/2004 | Bevilacqua et al. | |
| 2005/0032070 A1 | 2/2005 | Raimundo et al. | |
| 2008/0166357 A1 | 7/2008 | Golz et al. | |
| 2009/0298880 A1 | 12/2009 | Wolfgang et al. | |

FOREIGN PATENT DOCUMENTS

| | | | |
|---|---|---|---|
| WO | 0055624 A2 | 9/2000 | |
| WO | 0059486 A2 | 10/2000 | |
| WO | 0149883 A2 | 7/2001 | |
| WO | 0179554 A1 | 10/2001 | |
| WO | 0244994 A2 | 6/2002 | |
| WO | 0250283 A2 | 6/2002 | |
| WO | 02064141 A1 | 8/2002 | |
| WO | 02099118 A2 | 12/2002 | |
| WO | 03017946 A2 | 3/2003 | |
| WO | 03020707 A1 | 3/2003 | |
| WO | 03038123 A2 | 5/2003 | |
| WO | 03054226 A3 | 7/2003 | |
| WO | 2004006886 A2 | 1/2004 | |
| WO | 2004009760 A2 | 1/2004 | |
| WO | 2004009760 A3 | 1/2004 | |
| WO | 2004074456 A2 | 9/2004 | |
| WO | 2006039663 A2 | 4/2006 | |
| WO | 2008121899 A2 | 10/2008 | |
| WO | 2008144599 A2 | 11/2008 | |
| WO | 2010030783 A1 | 3/2010 | |

OTHER PUBLICATIONS

Alfaro, C.L. et al. Journal of Clinical Pharmacology 40:58-66 (2000).*
Cheer, S.M. and Goa, K.L. Drugs 61(1):81 (2001).*
Bradford, "CYP2D6 Allele Frequency in European Caucasians, Asians, Africans and Their Descendants", pp. 229-243, Ashley Publications Ltd. ISSN 1452-2416, Pharmacogenomics 2002vol. 3 No. 2.
Bertilsson et al., "Molecular Genetics of CYP2D6: Clinical Relevance with Focus on Psychotropic Drugs", 2002 pp. 111-122, Blackwell Science Ltd.
Chainuvati et al., "Combined Phenotypic Assessment of Cytochrome p450, 1A2, 2C9, 2C19, 2D6, and 3A, N-acetyltransferase-2 and Xanthine Oxidase Activities with the Cooperstown 5+1 Cocktail", Clinical Pharmacology and Therapeutics, Nov. 2003, vol. 74, No. 5.
Dahl et al., "Genetic Analysis of the CYP2D Locus in Relation to Debrisoquine Hydroxylation Capacity in Korean, Japanese, and Chinese Subjects", Pharmacogenetics, 1995, pp. 159-164, vol. 5.
Gough et al., "Identification of the Primary Gene Defect at the Cytochrome P 450 CYP2D Locus", Nature, Oct. 25, 1990, pp. 773-776, vol. 374.

(Continued)

*Primary Examiner* — Diana B Johannsen
(74) *Attorney, Agent, or Firm* — Hoffman Warnick LLC

(57) ABSTRACT

The present invention relates to methods for treating a patient with iloperidone or a metabolite thereof, which patient is also being treated with fluoxetine, and lowering risk for QT prolongation.

1 Claim, No Drawings

(56) References Cited

OTHER PUBLICATIONS

Hanioka et al., The Human CYP2D Locus Associated with a Common Genetic Defect in Durg Oxidation: A G1934-A Base Change in Intron 3 of a Mutant CYP2D6 Allele Results in an Aberrant 3' Splice Recognition Site, American Journal of Human Genetics, 1990, pp. 994-1001, vol. 47.

Jaanson et al., Maintenance Therapy with Zuclopenthixol Decanoate: Associations Between Plasma Concentrations, Neurological Side Effects and CYP2D6 Genotype, Psychopharmacology, 2002, pp. 67-73, vol. 162.

Jain, "An Assessment of Iloperidone for the Treatment of Schizophrenia", Expert Opinion on Investigational Drugs, Dec. 2000, vol. 9, No. 12.

Johansson et al., "Genetic Analysis of the Chinese Cytochrome P4502D Locus: Characterization of Variant CYP2D6 Genes Present in Subjects with Diminished Capacity for Debrisoquine Hydroxylation", Molecular Pharmacology, Jun. 1994, pp. 452-459, vol. 46.

Kagimoto et al., "Multiple Mutations of the Human Cytochrome P450IID6 Gene (CYP2D6) in Poor Metabolizers of Debrisoquine", The Journal of Biological Chemistry, Oct. 1990, pp. 17209-17214, vol. 265, No. 28.

Kelleher et al., "Advances in Atypical Antipsychotics for the Treatment of Schizophrenia—New Formulations and New Agents", CNS, ADIS International, 2002, pp. 249-261, vol. 16, No. 4, Auckland, NZ.

Lyamichev et al., "Polymorphism Identification and Quantitative Detection of Genomic DNA by Invasive Cleavage of Oligonucleotide Probes", Nature Biotechnology, Mar. 1999, pp. 292-296, vol. 17.

McElroy et al., "CYP2D6 Genotyping as an Alternative to Phenotyping for Determination of Metabolic Status in a Clinical Trial Setting", AAPS Pharmsci 2000, Oct. 2000, pp. 1-11, vol. 2, No. 4, Article 33 (www.pharmsci.org).

Mutlib et al., "Application of Liquid Chromatography/Mass Spectrometry in Accelerating the Identification of Human Liver Cytochrome P450 Isoforms Involved in the Metabolism of Iloperidone", The Journal of Pharmacology and Experimental Therapeutics, May 1998, pp. 1285-1293.

Neville et al., "Characterization of Cytochrome P450 2D6 Alleles Using the Invader System", BioTechniques, Jun. 2002, vol. 32.

Subramanian et al., "Receptor Profile of P88-8991 and P95-12133, Metabolites of the Novel Antipsychotic Iloperidone", Progress in Neuro-Psychopharmacology & Biological Psychiatry, Mar. 2002, pp. 553-560, vol. 26, No. 3, England.

Yokota et al., "Evidence for a New Variant CYP2D6 Allele CYP2D6J in a Japanese Population Associated with Lower In Vivo Rates of Sparteine Metabolism", Pharmacogenetics, 1993, pp. 256-263, vol. 3.

Unknown et al., "Home Page of the Human Cytochrome P450 (CYP) Allele Nomenclature Committee", (www.cypalleles.ki.se/) May 2008, 2 pages, printed May 28, 2008.

Johannsen, Office Action Communication for U.S. Appl. No. 11/576,178 dated Sep. 29, 2011, 19 pages.

Johannsen, Office Action Communication for U.S. Appl. No. 11/576,178 dated Mar. 15, 2012, 24 pages.

Johannsen, Office Action Communication for U.S. Appl. No. 11/576,178 dated Dec. 20, 2012, 13 pages.

European Patent Office, European Search Report for Application No. EP12164353 dated Aug. 29, 2012, 13 pages.

Sheridan et al., "Empirical Regioselectivity Models for Human Cytochromes P450 3A4, 2D6, and 2C9," Jun. 2007, pp. 3173-3184, J. Med. Chem. vol. 50, American Chemical Society.

Ryan et al., "Non-PCR-Dependent Detection of the Factor V Leiden Mutation From Genomic DNA Using a Homogeneous Invader Microtiter Plate Assay," 1999, pp. 135-144, Molecular Diagnosis, vol. 4, No. 2.

Shimada et al., "Characterization of Bufuralol Hydroxylation Activities in Liver Microsomes of Japanese and Caucasian Subjects Genotyped for CYP2D6," 2001, pp. 143-156, Pharmacogenetics 2001.

Johannsen, Office Action Communication for U.S. Appl. No. 12/208,027 dated Mar. 30, 2011, 31 pages.

Johannsen, Notice of Allowance and Fee(s) Due for U.S. Appl. No. 11/576,178 dated Jul. 25, 2013, 18 pages.

Johannsen, Office Action Communication for U.S. Appl. No. 12/208,027 dated Aug. 31, 2011, 25 pages.

Johannsen, Office Action Communication for U.S. Appl. No. 12/208,027 dated Jul. 3, 2013, 22 pages.

Johannsen, Office Action Communication for U.S. Appl. No. 12/208,027 dated Dec. 20, 2012, 19 pages.

Patent Cooperation Treaty, Notificiation of Transmittal of the International Search Report and The Written Opinion of the International Searching Authority, or the Declaration for PCT/US2005/035526 dated Aug. 23, 2006, 11 pages.

Patent Cooperation Treaty, Notification of Transmittal of the International Preliminary Report on Patentability for PCT/US2005/035526 dated Jun. 8, 2007, 5 pages.

European Patent Office, Extended Search Report for Application No. 05803436.4 dated Feb. 25, 2008, 12 pages.

European Patent Office, Examination Report for Application No. 05803436.4 dated May 28, 2008, 1 page.

Johannsen, Office Communication Restriction Requirement for U.S. Appl. No. 11/576,178 dated Dec. 30, 2009, 7 pages.

Australian IP, Examination Report dated Jan. 12, 2011, Australian Application No. 2005292246, 2 pages.

Patent Cooperation Treaty, International Preliminary Report on Patentability of the International Searching Authority dated Mar. 24, 2011, International Application No. PCT/US2009/056517, 10 pages.

Johannsen, Final Office Action Communications for U.S. Appl. No. 11/576,178 Dated Feb. 17, 2011, 21 pages.

Johannsen, Office Action Summary for U.S. Appl. No. 11/576,178 dated May 3, 2010, 24 pages.

European Patent Office, Examination Report for Application No. 05803436.1 dated Apr. 21, 2010, 8 pages.

Fuselli et al., "Molecular diversity at the CYP2D6 locus in the Mediterranean region," Nov. 2004, pp. 916-924, European Journal of Human Genetics, vol. 12, No. 11, ISSN: 1018-4813.

Sachse et al., "Cytochrome P450 2D6 Variants in a Caucasian Population: Allele Frequencies and Phenotypic Consequences," Feb. 1997, pp. 284-295, American Journal of Human Genetics, vol. 60, No. 2, ISSN: 0002-9297.

Wang et al., "G169R Mutation Diminishes the Metabolic Activity of CYP2D6 in Chinese," Mar. 1999, pp. 385-388, Drug Metabolism and Disposition, vol. 27, No. 3, XP-001036785, ISSN: 0900-9558.

Raimundo et al., "A novel intronic mutation, 2988G>A, with high predictivity for impaired function of cytochrome P450 2D6 in white subjects," 2004, pp. 128-138, Clinical Pharmacology & Therapeutics, vol. 76, No. 2.

Gaedigk et al., "Delection of the Entire Cytochrome P450 CYP2D6 Gene as a Cause of Impaired Drug Metabolism in Poor Metabolizers of the Debrisoquine/Sparteine Polymorphism," 1991, pp. 943-950, Am. J. Hum. Genet., vol. 48.

Australian IP, Examination Report dated Nov. 13, 2009, Australian Application No. 2005292246, 2 pages.

Patent Cooperation Treaty, International Search Report and the Written Opinion of the International Searching Authority dated Nov. 27, 2009, International Application No. PCT/US2009/056517, 18 pages.

Caccia, "New Antipsychotic Agents for Schizophrenia: Pharmacokinetics and Metabolism Update", Jul. 2002, pp. 1073-1080, Current Opinion in Investigational Drugs, vol. 3, No. 7.

Complaint for Patent Infringement, *Vanda Pharmaceuticals Inc.* v. *Roxane Laboratories, Inc.*, C.A. No. 14-(22 pages) (US Dist. for the Dist. of Delaware filed Jun. 16, 2014).

Defendant's Motion to Dismiss, *Vanda Pharmaceuticals Inc.* v. *Roxane Laboratories, Inc.*, C.A. No. 14-757-GMS (4 pages) (US Dist. for the Dist. of Delaware filed Aug. 11, 2014).

Memorandum of Defendant Roxane Laboratories, Inc. In Support of Its Motion to Dismiss, C.A. No. 14-757-GMS (18 pages) (US Dist. for the Dist. of Delaware filed Aug. 11, 2014).

Vanda's Answering Brief in Opposition to Roxane's Motion to Dismiss, *Vanda Pharmaceuticals Inc.* v. *Roxane Laboratories, Inc.*, C.A. No. 14-757-GMS (25 pages) (US Dist. for the Dist. of Delaware filed Sep. 11, 2014).

(56) References Cited

OTHER PUBLICATIONS

Declaration of Mihael H. Polymeropoulos in Support of Vanda's Opposition to Roxane's Motion to Dismiss, *Vanda Pharmaceuticals Inc.* v. *Roxane Laboratories, Inc.*, C.A. No. 14-757-GMS (290 pages) (US Dist. for the Dist. of Delaware filed Sep. 11, 2014).

Reply Memorandum of Defendant Roxane Laboratories, Inc. In Support of Its Motion to Dismiss, *Vanda Pharmaceuticals Inc.* v. *Roxane Laboratories, Inc.*, C.A. No. 14-757-GMS (15 pages) (US Dist. for the Dist. of Delaware filed Sep. 29, 2014).

Novartis Pharmaceuticals Corporation, Fanapt Full Prescribing Information (20 pages) (Apr. 2014).

Janssen Pharmaceutica Products, L.P., Risperdal(R) (Risperidone) tablets/oral solution; Risperdal(R) M-TAB(TM) (Risperidone) Orally Disintegrating Tablets (34 pages) (Dec. 2003).

Janssen Pharmaceuticals, Inc., Risperdal Full Prescribing Information (58 pages) (Apr. 2014).

Janssen Pharmaceuticals, Inc., Risperdal Full Prescribing Information (57 pages) (Revised Jul. 2012, accepted by the US FDA Aug. 2012).

Janssen Pharmaceuticals, Inc., Risperdal Full Prescribing Information (57 pages) (Sep. 2011).

Vanda Pharmaceuticals Inc., Fanapt (iloperidone) Tablets Full Prescribing Information (23 pages) (May 2009).

Gough et al., "Identification of the Primary Gene Defect at the Cytochrome P 450 CYP2D Locus", Nature, Oct. 25, 1990, pp. 773-776, vol. 347.

Johannsen, Office Action Communication for U.S. Appl. No. 14/060,978 dated Jun. 5, 2014, 48 pages.

Roden, "Drug-induced prolongation of the QT interval," N Engl J Med. 350(10):1013-22 (2004).

Office Action for Canadian Patent Application No. 2,582,022, dated Apr. 28, 2015, CA (4 pages).

\* cited by examiner

SEQUENCE LISTING

```
<160> NUMBER OF SEQ ID NOS: 6

<210> SEQ ID NO 1
<211> LENGTH: 19
<212> TYPE: DNA
<213> ORGANISM: Artificial Sequence
<220> FEATURE:
<223> OTHER INFORMATION: Primer for amplifying CYP2D6 Exons 1 and 2

<400> SEQUENCE: 1
ctgggctggg agcagcctc                                                        19

<210> SEQ ID NO 2
<211> LENGTH: 23
<212> TYPE: DNA
<213> ORGANISM: Artificial Sequence
```

```
<220> FEATURE:
<223> OTHER INFORMATION: Primer for amplifying CYP2D6 Exons 1 and 2

<400> SEQUENCE: 2
cactcgctgg cctgtttcat gtc                                              23

<210> SEQ ID NO 3
<211> LENGTH: 22
<212> TYPE: DNA
<213> ORGANISM: Artificial Sequence
<220> FEATURE:
<223> OTHER INFORMATION: Primer for amplifying CYP2D6 Exons 3, 4, 5 and
      6

<400> SEQUENCE: 3
ctggaatccg gtgtcgaagt gg                                               22

<210> SEQ ID NO 4
<211> LENGTH: 20
<212> TYPE: DNA
<213> ORGANISM: Artificial Sequence
<220> FEATURE:
<223> OTHER INFORMATION: Primer for amplifying CYP2D6 Exons 3, 4, 5 and
      6

<400> SEQUENCE: 4
ctcggcccct gcactgtttc                                                  20

<210> SEQ ID NO 5
<211> LENGTH: 22
<212> TYPE: DNA
<213> ORGANISM: Artificial Sequence
<220> FEATURE:
<223> OTHER INFORMATION: Primer for amplifying CYP2D6 Exons 7, 8 and 9

<400> SEQUENCE: 5
gaggcaagaa ggagtgtcag gg                                               22

<210> SEQ ID NO 6
<211> LENGTH: 23
<212> TYPE: DNA
<213> ORGANISM: Artificial Sequence
<220> FEATURE:
<223> OTHER INFORMATION: Primer for amplifying CYP2D6 Exons 7, 8 and 9

<400> SEQUENCE: 6
agtcctgtgg tgaggtgacg agg                                              23
```

METHODS FOR THE ADMINISTRATION OF ILOPERIDONE

CROSS-REFERENCE TO RELATED APPLICATIONS

This application is a continuation of U.S. patent application Ser. No. 14/060,978, filed Oct. 23, 2013, now abandoned, which is a continuation of U.S. patent application Ser. No. 11/576,178, filed Mar. 28, 2007 (now U.S. Pat. No. 8,586, 610, issued Nov. 19, 2013), which is a 35 U.S.C. §371 national stage entry of International Patent Application No. PCT/US2005/035526, filed Sep. 30, 2005, which claims the benefit of U.S. Provisional Patent Application No. 60/614, 798, filed Sep. 30, 2004. Each of the foregoing patent applications is incorporated herein.

SEQUENCE LISTING

The sequence listing contained in the electronic file titled "VAND-0002-US-CON2SeqID_2014-08-29," created Aug. 29, 2014, comprising 14 KB, is hereby incorporated herein by reference.

BACKGROUND OF THE INVENTION

Several genes associated with drug metabolism have been found to be polymorphic. As a result, the abilities of individual patients to metabolize a particular drug may vary greatly. This can prove problematic or dangerous where an increased concentration of a non-metabolized drug or its metabolites is capable of producing unwanted physiological effects.

The cytochrome P450 2D6 gene (CYP2D6), located on chromosome 22, encodes the Phase I drug metabolizing enzyme debrisoquine hydroxylase. A large number of drugs are known to be metabolized by debrisoquine hydroxylase, including many common central nervous system and cardiovascular drugs. One such drug is iloperidone (1-[4-[3-[4-(6-fluoro-1,2-benzisoxazol-3-yl)-1-piperidinyl]propoxy]-3-methoxyphenyl]ethanone). Iloperidone and methods for its production and use as an antipsychotic and analgesic are described in U.S. Pat. No. 5,364,866 to Strupczewski et al. The diseases and disorders that can be treated by administration of iloperidone include all forms of schizophrenia (i.e., paranoid, catatonic, disorganized, undifferentiated, and residual), schizoaffective disorders, bipolar mania/depression, cardiac arrhythmias, Tourette's Syndrome, brief psychotic disorder, delusional disorder, psychotic disorder NOS (not otherwise specified), psychotic disorder due to a general medical condition, schizophreniform disorder, and substance-induced psychotic disorder. P88 is an active metabolite of iloperidone. See, e.g., PCT WO2003020707, which is incorporated herein by reference.

Among the unwanted physiological effects associated with an increased concentration of iloperidone or its metabolites is prolongation of the electrocardiographic QT interval. Mutations in the CYP2D6 gene have been associated with a number of drug metabolism-related phenotypes. These include the ultra rapid metabolizer (UM), extensive metabolizer (EM), intermediate metabolizer (IM), and poor metabolizer (PM) phenotypes. Where a particular drug is capable of producing unwanted physiological effects in its metabolized or non-metabolized forms, it is desirable to determine whether a patient is a poor metabolizer of the drug prior to its administration.

A number of references are directed toward the identification of CYP2D6 mutations and their corresponding phenotypes. For example, United States Patent Application Publication No. 2003/0083485 to Milos et al. describes a novel CYP2D6 variant associated with the PM phenotype and methods for assessing whether an individual possesses the variant prior to the administration of a drug. United States Patent Application Publication No. 2004/0072235 to Dawson describes a primer set useful in identifying variants of the CYP2D6 gene. Similarly, United States Patent Application Publication No. 2004/0091909 to Huang describes methods for screening an individual for variants in the CYP2D6 gene and other cytochrome P450 genes and tailoring the individual's drug therapy according to his or her phenotypic profile. Finally, United States Patent Application Publication No. 2004/0096874 to Neville et al. describes methods for identifying cytochrome P450 variants.

SUMMARY OF THE INVENTION

The present invention comprises the discovery that treatment of a patient, who has lower CYP2D6 activity than a normal person, with a drug that is pre-disposed to cause QT prolongation and is metabolized by the CYP2D6 enzyme, can be accomplishing more safely by administering a lower dose of the drug than would be administered to a person who has normal CYP2D6 enzyme activity. Such drugs include, for example, dolasetron, paroxetine, venlafaxin, and iloperidone. Patients who have lower than normal CYP2D6 activity are herein referred to as CYP2D6 Poor Metabolizers.

This invention also relates to methods for the identification of genetic polymorphisms that may be associated with a risk for QT prolongation after treatment with compounds metabolized by the CYP2D6 enzyme, particularly iloperidone or an active metabolite thereof or a pharmaceutically acceptable salt of either (including, e.g., solvates, polymorphs, hydrates, and stereoisomers thereof), and related methods of administering these compounds to individuals with such polymorphisms.

The present invention describes an association between genetic polymorphisms in the CYP2D6 locus, corresponding increases in the concentrations of iloperidone or its metabolites, and the effect of such increases in concentrations on corrected QT (QTc) duration relative to baseline. Any number of formulas may be employed to calculate the QTc, including, for example, the Fridericia formula (QTcF) and the Bazett formula (QTcB), among others. The present invention includes any such formula or method for calculating a QTc.

A first aspect of the invention provides a method for treating a patient with iloperidone or an active metabolite thereof or a pharmaceutically acceptable salt of either, comprising the steps of determining the patient's CYP2D6 genotype and administering to the patient an effective amount of iloperidone or an active metabolite thereof or a pharmaceutically acceptable salt of either based on the patient's CYP2D6 genotype, such that patients who are CYP2D6 poor metabolizers receive a lower dose than patients who are CYP2D6 normal metabolizers.

Another aspect of the invention provides a method for treating a patient who is a CYP2D6 poor metabolizer with iloperidone or an active metabolite thereof or a pharmaceutically acceptable salt of either, wherein the patient is administered a lower dosage than would be given to an individual who is not a CYP2D6 poor metabolizer.

Another aspect of the invention provides a method of treating a patient with iloperidone or an active metabolite thereof or a pharmaceutically acceptable salt of either comprising the steps of determining whether the patient is being administered a CYP2D6 inhibitor and reducing the dosage of drug if the patient is being administered a CYP2D6 inhibitor.

Another aspect of the invention provides a method for determining a patient's CYP2D6 phenotype comprising the steps of administering to the patient a quantity of iloperidone or an active metabolite thereof or a pharmaceutically acceptable salt of either, determining a first concentration of at least one of iloperidone and an iloperidone metabolite in the patient's blood, administering to the patient at least one CYP2D6 inhibitor, determining a second concentration of at least one of iloperidone and an iloperidone metabolite in the patient's blood, and comparing the first and second concentrations.

Another aspect of the invention provides a method for determining whether a patient is at risk for prolongation of his or her QTc interval due to iloperidone administration comprising the step of: determining a patient's CYP2D6 metabolizer status by either determining the patient's CYP2D6 genotype or CYP2D6 phenotype. In the case that a patient is determined to be at risk for prolongation of his or her QTc interval, the dose of iloperidone administered to the patient may be reduced.

Another aspect of the invention provides a method of administering iloperidone or an active metabolite thereof, or a pharmaceutically acceptable salt of either, for the treatment of a disease or disorder in a human patient comprising the steps of determining the activity of the patient's CYP2D6 enzyme on at least one of iloperidone and its metabolites relative to the activity of a wild type CYP2D6 enzyme and reducing the dose of at least one of iloperidone and its pharmaceutically acceptable salts if the patient's CYP2D6 enzyme activity is less than that of the wild type CYP2D6.

Another aspect of the invention relates to modifying the dose and/or frequency of dosing with iloperidone or a pharmaceutically acceptable salt thereof based on the P88:P95 ratio and/or the (P88+iloperidone):P95 ratio in a blood sample of a patient being treated with iloperidone or P88, especially patients susceptible to QT prolongation or to harmful effects associated with QT prolongation.

Another aspect of the invention provides a kit for use in determining a CYP2D6 genotype of an individual, comprising a detection device, a sampling device, and instructions for use of the kit.

Another aspect of the invention provides a kit for use in determining a CYP2D6 phenotype of an individual, comprising a detection device, a collection device, and instructions for use of the kit.

Another aspect of the invention provides a kit for use in determining at least one of a P88 to P95 ratio and a P88 and iloperidone to P95 ratio in an individual, comprising a detection device, a collection device, and instructions for use of the kit.

Yet another aspect of the invention provides a method for commercializing a pharmaceutical composition comprising at least one of iloperidone, a pharmaceutically acceptable salt of iloperidone, an active metabolite of iloperidone, and a pharmaceutically acceptable salt of an active metabolite of iloperidone, said method comprising: obtaining regulatory approval of the composition by providing data to a regulatory agency demonstrating that the composition is effective in treating humans when administered in accordance with instructions to determine whether or not a patient is a CYP2D6 poor metabolizer prior to determining what dose to administer to the patient; and disseminating information concerning the use of such composition in such manner to prescribers or patients or both.

The foregoing and other features of the invention will be apparent from the following more particular description of embodiments of the invention.

DETAILED DESCRIPTION OF THE INVENTION

Iloperidone is a benzisoxazole-piperidinyl derivative, currently in development for the treatment of CNS disorders. Data from placebo-controlled Phase III studies of iloperidone showed a Fridericia correction of QT duration (QTcF) increase of 0.1 to 8.5 msec at doses of 4-24 mg, when comparing a single ECG at baseline to a single ECG at endpoint. At lower doses of iloperidone (4 mg-16 mg) QTcF prolongation was minimal (0.1-5 msec). In the most recent study, a greater prolongation was observed when higher doses of iloperidone (20-24 mg/day) were studied. The mean change in the QTcF at doses 20-24 mg/day was 8.5 msec, and 4.6 msec in the 12-16 mg/day dose range in this study. These data suggest that treatment with iloperidone can be associated with prolongation of the QT interval similar to other drugs in this class, and that the effect may be dose sensitive in the clinical dose range.

The research leading to the present invention was designed to examine the effect of different doses of iloperidone relative to the effect of ziprasidone and quetiapine on QTc duration under carefully controlled conditions. To further evaluate the possible relationship between exposure to iloperidone and the comparators to QTc duration, reassessment after pharmacological inhibition of the principle metabolic pathways for each drug, under steady-state conditions, was also planned.

Blood samples for pharmacogenetic analysis were collected at screening. Two polymorphisms previously associated with poor metabolizing status were genotyped in the CYP2D6 locus and 251 genotypes were collected. The individual genotypes were studied for detection of association between genotype class and concentrations of iloperidone and its metabolites P88 and P95. The functional effect of the polymorphisms was also evaluated by analyzing the effect of the addition of the CYP2D6 inhibitor paroxetine on the concentrations of the parent drug and its metabolites.

The research leading to the present invention identified a significant association between CYP2D6 genotype and concentrations of P88 before the addition of inhibitors as well as the effect of this association on QTc prolongation.

Iloperidone is a substrate for two P450 enzymes; CYP2D6 and CYP3A4. Most metabolic clearance of iloperidone depends on these two enzymes. CYP2D6 catalyzes hydroxylation of the pendant acetyl group to form metabolite P94, which is converted to P95 after some additional reactions. Addition of the CYP2D6 inhibitor fluoxetine, along with iloperidone resulted in increases of the area under the curve (AUC) for iloperidone and P88 of 131% and 119% respectively. Addition of the CYP3A4 inhibitor ketoconazole in interaction studies resulted in a 38-58% increase in the concentrations of iloperidone and its main metabolites P88 and P95. P88 has a pharmacological profile including affinity for the HERG channel similar to that of iloperidone. P95 is less lipophilic and is dissimilar in its binding profile compared to iloperidone, including having very low affinity for the HERG channel. For these reasons P95 is regarded as being pharmacologically inactive.

The addition of metabolic inhibitors in this study therefore allowed for an evaluation of the effect of increasing blood-concentration of iloperidone and/or its metabolites on QT duration. More specifically, this study allowed for an evaluation of the effect of iloperidone on QTc before and after the addition of the CYP2D6 inhibitor, paroxetine, as well as before and after the addition of the CYP3A4 inhibitor, ketoconazole.

The CYP2D6 gene is highly polymorphic, with more than 70 allelic variants described so far. Most embodiments of the present invention concern the two most common polymorphisms within the CYP2D6 gene in Caucasian populations, CYP2D6G1846A and CYP2D6P34S (also referred to as CYP2D6C100T). These polymorphisms correspond to nucleotides 3465 and 1719, respectively, in GenBank sequence M33388.1 (GI:181303). The CYP2D6P34S/CYP2D6C100T polymorphism also corresponds to nucleotide 100 in GenBank mRNA sequence M20403.1 (GI: 181349).

The CYP2D6G1846A polymorphism (known as the CYP2D6*4 alleles, encompassing *4A, *4B, *4C, *4D, *4E, *4F, *4G, *4H, *4J, *4K, and *4L) represents a G to A transition at the junction between intron 3 and exon 4, shifting the splice junction by one base pair, resulting in frameshift and premature termination of the protein (Kagimoto 1990, Gough 1990, Hanioka 1990). The CYP2D6P34S/CYP2D6C100T polymorphism (known as the CYP2D6*10 and CYP2D6*14 alleles) represents a C to T change that results in the substitution of a Proline at position 34 by Serine (Yokota 1993, Johansson 1994). Both of these polymorphisms have been associated with reduced enzymatic activity for different substrates (Johansson 1994, Dahl 1995, Jaanson 2002, see also review by Bertilsson 2002)

Methods

A. Samples 128 individuals consented to the pharmacogenetic study. Blood samples were collected according to the pharmacogenetics protocol and after the consent of patients. The DNA was extracted from whole blood by Covance using the PUREGENE DNA isolation kit (D-50K).

The 128 individuals that participated were a good representation of the total sample of 165 individuals that participated in the trial. 22 of 29 total were from the iloperidone 8 mg bid group, 30 of 34 were from the iloperidone 12 mg bid group, 22 of 31 from the 24 mg qd group, 3 of 5 of the risperidone group, 28 of 33 of the ziprazidone group, and 23 of 33 of the quetiapine group.

B. Genotyping

Genotypes for the CYP2D6G1846A polymorphism were ascertained for 123 of the 128 consenting individuals, while genotypes for the CYP2D6C100T polymorphism were identified for all 128 participants. Genotyping was performed on amplified DNA fragments. The CYP2D6 genomic region was amplified using a triplex PCR strategy (Neville 2002). In brief, primers used were:

```
Exons 1 & 2  SEQ. ID. 12D6L1F1:  CTGGGCTGGGAGCAGCCTC,
             SEQ. ID. 22D6L1R1:  CACTCGCTGGCCTGTTT-
                                 CATGTC,
Exons 3,     SEQ. ID. 32D6L2F:   CTGGAATCCGGTGTCGAA
4,
5 & 6                            GTGG,
             SEQ. ID. 42D6L2R2:  CTCGGCCCCTGCACTGT
                                 TTC,
Exons 7,     SEQ. ID. 52D6L3F:   GAGGCAAGAAGGAGTGT
8 &
9                                CAGGG,
             SEQ. ID. 62D6L3R5B: AGTCCTGTGGTGAGGTGA
                                 CGAGG,
```

Amplification was performed on 40-100 ng of genomic DNA using a GC-rich PCR kit (Roche Diagnostics, Mannheim, Germany) according to the manufacturer's recommendations. Thermocycling conditions were as follows: initial denaturation (3 min 95° C.), 10 cycles of 30 s of denaturation (30 s at 95° C.), annealing (30 s at 66° C.), and extension, (60 s at 72° C.) followed by 22 cycles: 30 s at 95° C., 30 s at 66° C., 60 s+5 s/cycle at 72° C. A final extension followed (7 min at 72° C.).

Third Wave Technologies, Inc (Madison, Wis.) developed the probe sets for genotyping. Genotyping was performed on PCR products using the Invader® assay (Lyamichev 1999) (Third Wave Technologies, Inc) according to the manufacturer's recommendations.

The genotypes of individuals distributed among the three iloperidone groups were not significantly different (Table 1A and 1B).

TABLE 1A

Genotype frequencies by iloperidone dose class for CYP2D6C100T

| Iloperidone dose group | Genotype | | | |
|---|---|---|---|---|
| | CC | CT | TT | Total |
| Ilo 8 mg bid | 19[a] | 2 | 1 | 22 |
| Ilo 12 mg bid | 23 | 6 | 1 | 30 |
| Ilo 24 mg qd | 15 | 6 | 1 | 22 |
| Total | 57 | 14 | 3 | 74 |

[a]number of individuals

TABLE 1B

Genotype frequencies by iloperidone dose class for CYP2D6G1846A

| Iloperidone dose group | Genotype | | | |
|---|---|---|---|---|
| | AA | AG | GG | Total |
| Ilo 8 mg bid | 0 | 3 | 17 | 20 |
| Ilo 12 mg bid | 1 | 6 | 23 | 30 |
| Ilo 24 mg qd | 1 | 5 | 15 | 21 |
| Total | 2 | 14 | 55 | 71 |

C. Statistical Analysis

The genotype effect of the two CYP2D6 polymorphisms on period 1 concentrations was evaluated using the following ANOVA model. Concentrations of iloperidone, P88, and P95 at Period 1, without inhibitor, at the time at which maximum blood concentration of the parent compound or metabolite was reached (Tmax) were used as the dependent variable, the genotypes of each polymorphism as classes and the treatment as a covariate. In order to adjust for treatment effects after the single dose of iloperidone, the 8 mg bid was coded as 8, the 12 mg bid as 12 and the 24 mg qd as 24.

The function of these polymorphisms on the degree of inhibition of the CYP2D6 enzyme was calculated from the ratio of concentrations of P88 and P95 in period 2, after the addition of the inhibitor of CYP2D6. The concentrations of iloperidone and/or its metabolites (e.g., P88 and P95) may be determined in period 1 and/or period 2 by any known or later-developed method or device, including titration.

Results and Discussion

In order to understand the functional significance of the two CYP2D6 polymorphisms on the activity of the enzyme, we examined the association of the various genotypes with the relative concentrations of the metabolites P88 and P95. It is known that P88 is degraded by CYP2D6 and that CYP2D6 is involved in the synthesis of P95. The relative amounts of P88 and P95 would therefore be controlled by the activity of the CYP2D6 enzyme. We calculated the ratio of P88/P95 before inhibition in Period 1 and at the Tmax of the two metabolites, as well as the ratio of P88/P95 in Period 2 after the addition of the CYP2D6 inhibitor paroxetine. In individuals with the wild type enzyme the concentration of P88 is expected to increase in Period 2, while in the same period the concentration of P95 is expected to decline.

For Period 1 the mean P88/P95 ratio among the 91 iloperidone treated patients was equal to 1.0 with a range from 0.14 to 8.19. Among the same individuals for Period 2 the mean ratio was 2.4 with a range from 0.5 to 8.49. The mean ratio of the ratios Period 1/Period 2 was equal to 0.37 with a range from 0.11 to 2.75.

Among the genotyped individuals the values were similar with means of 1, 2.45 and 0.37 for Period 1, Period 2 and Period 1/Period 2 respectively, indicating no sample bias. For polymorphism CYP2D6G1846A the means were significantly different between the three-genotype classes AA, AG and GG. For AA the respective values were 6.1, 3.41, and 1.89, for AG they were 2.4, 4.2, and 0.52 and for GG 0.57, 1.94 and 0.28 (Table 2).

TABLE 2

Ratios of P88, P95 concentrations according to genotype

| Population | P88/P95 Period1 | P88/P95 Period 2 | P88/P95 (Period1/ Period2) |
|---|---|---|---|
| All | 1.0 (0.14-8.19) | 2.45 (0.50-8.49) | 0.37 (0.11-2.75) |
| | | CYP2D6G1846A | |
| AA | 6.1 (3.96-8.19) | 3.41 (2.96-3.87) | 1.89 (1.0-2.75) |
| AG | 2.4 (0.44-7.0) | 4.20 (2.2-7.57) | 0.52 (0.14-1.28) |
| GG | 0.57 (0.14-2.2) | 1.94 (0.52-4.71) | 0.28 (0.11-0.61) |

The differences between genotype classes were significant at the p<0.0001 level in ANOVA test. These data suggest that the AA class represent a CYP2D6 poor metabolizer as indicated by the high ratio of P88/P95 in period 1 and the relatively small effect of the addition of the inhibitor in Period 2. The AG class seems to exhibit an intermediate phenotype between the poor metabolizer and the wild type with an approximately 2-fold reduction of the CYP2D6 activity after the addition of the inhibitor, as indicated by the ratio of the ratios (Table 2). This analysis provides a phenotypic characterization of the CYP2D6G1846A polymorphism as it relates to the metabolism of iloperidone.

Having established a functional role of this polymorphism, we calculated the concentrations of P88 at Period 1 at the Tmax of P88 for each genotype class. P88 concentrations were significantly (p<0.005) higher for the AA and AG classes as compared to the GG class for each of the three iloperidone dose groups (Table 3).

TABLE 3

P88 concentrations in Period 1 according to CYP2D6 genotype

| Genotype | N obs | LSMeans | P value |
|---|---|---|---|
| AA | 2 | 62.70 | <0.0001 |
| AG | 14 | 31.40 | |
| GG | 55 | 21.03 | |
| TRT dose | | | 0.0015 |
| CYP2D6G1846A *TRT dose | | | 0.0058 |

Although the number of individuals carrying the A allele is limited, the results obtained in the study consistently suggest that individuals of the AA and AG class are expected to experience higher concentrations of P88 at Tmax as compared with GG individuals. Similar results were obtained with polymorphism CYP2D6C100T (Table 4 and 5).

TABLE 4

Ratios of P88, P95 concentrations according to genotype

| Population | P88/P95 Period1 | P88/P95 Period 2 | P88/P95 (Period1/ Period2) |
|---|---|---|---|
| All | 1.0 (0.14-8.19) | 2.45 (0.50-8.49) | 0.37 (0.11-2.75) |
| | | CYP2D6C100T | |
| CC | 0.6 (0.14-2.28) | 1.93 (0.52-4.71) | 0.27 (0.11-0.61) |
| CT | 2.2 (0.44-7.0) | 4.14 (2.2-7.57) | 0.49 (0.14-1.28) |
| TT | 5.24 (3.56-8.19) | 4.19 (2.96-5.74) | 1.46 (0.62-2.75) |

TABLE 5

P88 concentrations in Period 1 according to CYP2D6 genotype

| Genotype | N obs | LSMeans | P value |
|---|---|---|---|
| CC | 57 | 21.03 | |
| CT | 14 | 33.16 | <0.0001 |
| TT | 3 | 51.00 | |
| TRT dose | | | <0.0001 |
| CYP2D6C100T*TRT dose | | | 0.0015 |

This result is expected given the fact that this polymorphism is in almost complete linkage disequilibrium with the CYP2D6G1846A polymorphism.

In order to understand whether the difference in concentration of P88 at Period 1 Tmax was relevant to the increases in QTc after the addition of the inhibitors, we used the observed mean of P88 for the CYP2D6G1846A AG group to divide all individuals into two classes. The first includes individuals with P88 concentrations at Period 3, after the addition of both inhibitors, of equal to or less than 34 ng/mL and the second class includes individuals with P88 concentration greater than 34 ng/mL. We then compared the two classes in regards to the QTc change from baseline at Period 3. Using an ANOVA statistic for the first class P88>34 (n=55) the QTc mean change from baseline in Period 3 was 22.7 msec and that for P88≤34 (n=12) the mean QTc for the same period was 7.7 msec. The QTc changes from baseline for Period 1 and Period 2 according to genotype and iloperidone dose are given in Table 6 and 7.

TABLE 6

QTc change at Period 1 according to CYP2D6 genotype and iloperidone dose

| | iloperidone Dose | | |
|---|---|---|---|
| Genotype | 8 mg bid | 12 mg bid | 24 mg qd |
| | CYP2D6G1846A | | |
| AA | | 17.7 (1)[a] | 38.4 (1) |
| AG | -0.8 (3) | 5.8 (6) | 19.0 (5) |
| GG | 7.8 (17) | 11.8 (23) | 14.0 (14) |
| | CYP2D6C100T | | |
| TT | -8.4 (1) | 17.7 (1) | 38.4 (1) |
| CT | 2.9 (2) | 5.8 (6) | 19.0 (5) |
| CC | 7.8 (17) | 11.8 (23) | 9.5 (14) |

[a]number of individuals

TABLE 7

QTc change at Period 2 according to
CYP2D6 genotype and iloperidone dose

| Genotype | iloperidone dose | | |
|---|---|---|---|
| | 8 mg bid | 12 mg bid | 24 mg qd |
| CYP2D6G1846A | | | |
| AA | | 25.0 (1) | 28.4 (1) |
| AG | 8.1 (3) | 8.7 (6) | 20.6 (5) |
| GG | 11.7 (18) | 14.5 (21) | 16.4 (15) |
| CYP2D6C100T | | | |
| TT | −0.7 (1) | 25.0 (1) | 28.4 (1) |
| CT | 12.5 (2) | 8.7 (6) | 20.6 (5) |
| CC | 11.7 (16) | 14.5 (21) | 16.4 (15) |

These results however should be viewed with caution since the number of observations is small. If one was, however, to focus on the iloperidone 24 mg qd, there is a trend for higher QTc among AA, and AG individuals for CYP2D6G1846A as compared to GG. This difference disappears after the addition of the CYP2D6 inhibitor in Period 2.

These observations suggest that the differences in P88 concentrations during Period 1 between the different classes of genotypes may be relevant to QTc changes from baseline. Given the small number of observations and the unbalanced in regards to genotype design of the study, a confirmatory prospectively designed study may be required before any further interpretation of this data is warranted. Notwithstanding these caveats, the results discussed above show that patients can be more safely treated with iloperidone if the dose of iloperidone is adjusted based on the CYP2D6 genotype of each patient. For example, if a patient has a genotype which results in decreased activity of the CYP2D6 protein relative to the wild type CYP2D6, then the dose of iloperidone administered to such patient would be reduced to, for example, 75% or less, 50% or less, or 25% or less of the dose typically administered to a patient having a CYP2D6 genotype that results in a CYP2D6 protein that has the same or substantially the same enzymatic activity on P88 as the wild type CYP2D6 genotype/protein. For example, where the normal dosage of iloperidone or other CYP2D6-metabolized compound administered to an individual is 24 mg per day, an individual with a genotype associated with decreased CYP2D6 activity may receive a reduced dosage of 18, 12, or 6 mg per day.

Decreased CYP2D6 activity may be the result of other mutations. In particular, it is noted that the CYP2D6*2A mutation includes a CYP2D7 gene conversion in intron 1. In some cases, the lower CYP2D6 activity in a CYP2D6 poor metabolizer may be due to factors other than genotype. For example, a patient may be undergoing treatment with an agent, e.g., a drug that reduces CYP2D6 activity.

QTc prolongation is correlated to the ratios of P88/P95 and (iloperidone+P88)/P95. The mean ratios among CYP2D6 extensive metabolizers were 0.57 and 1.00, respectively. As shown above in Tables 3 and 5, CYP2D6 poor metabolizers have elevated P88 levels compared to CYP2D6 extensive metabolizers.

As CYP2D6 poor metabolizers comprise approximately 15% of the population, it was found that approximately 15% of those studied exhibited a P88/P95 ratio greater than 2.0 while the remaining 85% exhibited P88/P95 ratios less than 2.0. Table 8 below shows the least squares mean change in QTc for each dosage group. While the results for some groups are not statistically significant, they do indicate a trend supporting the hypothesis that QTc prolongation is correlated to P88/P95 ratio. Similar results were obtained when cutoff ratios of 3.0 and 4.0 were analyzed, providing further support to the hypothesis that the extent of QTc prolongation a patient may experience after treatment can be predicted by measuring P88 and P95 blood levels.

TABLE 8

Mean QTc Prolongation According to P88/P95 Ratio

| P88/P95 Ratio | LSMean QTc change from Baseline 8 mg bid | LSMean QTc change from Baseline 12 mg bid | LSMean QTc change from Baseline 8 + 12 mg bid | LSMean QTc change from Baseline 24 qd | LSMean QTc change from Baseline All Treatment Groups |
|---|---|---|---|---|---|
| <2 | 7.2 (n = 23) | 8.7 (n = 31) | 8.3 (n = 54) | 13.9 (n = 24) | 10.244 (n = 78) |
| >2 | 21.3 (n = 5) | 17.4 (n = 3) | 18.3 (n = 8) | 29.4 (n = 5) | 21.111 (n = 13) |
| P value | 0.0725 | 0.392 | 0.0815 | 0.0329 | 0.0131 |

Similar results were observed when considering QTc correlation to the (iloperidone+P88)/P95 ratio. Again, as approximately 15% of the population are CYP2D6 poor metabolizers, it was found that approximately 15% of those studied exhibited (iloperidone+P88)/P95 ratios greater than 3.0 while the remaining 85% exhibited ratios less than 3.0. Table 9 below shows the least squares mean change in QTc for each dosage group. While the results for some groups are not statistically significant, they do indicate a trend supporting the hypothesis that QTc prolongation is correlated to (iloperidone+P88)/P95 ratio. Indeed, when cutoff ratios of 4 and higher were analyzed, similar results were obtained providing further support to the hypothesis that the extent of QTc prolongation a patient may experience after treatment can be predicted by measuring iloperidone, P88 and P95 blood levels.

TABLE 9

Mean QTc Prolongation According to (iloperidone + P88)/P95 Ratio

| (ILO + P88)/ P95 Ratio | LSMean QTc change from Baseline 8 mg bid | LSMean QTc change from Baseline 12 mg bid | LSMean QTc change from Baseline 8 + 12 mg bid | LSMean QTc change from Baseline 24 qd | LSMean QTc change from Baseline All Treatment Groups |
|---|---|---|---|---|---|
| <3 | 7.2 | 8.7 | 8.3 | 14.4 | 10.424 |
|  | (n = 23) | (n = 31) | (n = 54) | (n = 24) | (n = 78) |
| >3 | 21.3 | 15.2 | 17.3 | 30.5 | 20.031 |
|  | (n = 5) | (n = 3) | (n = 8) | (n = 5) | (n = 13) |
| P value | 0.0725 | 0.4223 | 0.0857 | 0.0522 | 0.0278 |

The starting point for determining the optimum dose of iloperidone is, as discussed above, a dose that has been shown to be acceptably safe and effective in patients having a CYP2D6 genotype that results in a protein having the same activity on iloperidone and P88 as the wild type CYP2D6 protein. Such doses are known in the art and are disclosed, for example, in U.S. Pat. No. 5,364,866 discussed above.

Generally, the dose of iloperidone administered to a patient will be decreased, as discussed above, if the enzymatic activity of the CYP2D6 enzyme on iloperidone and P88 is less than about 75% of that of the wild type CYP2D6. Enzymatic activity may be determined by any number of methods, including, for example, measuring the levels of iloperidone and/or P88 in an individual's blood. In such a case, the iloperidone dose can be lowered such that measured levels of iloperidone and/or P88 are substantially the same as levels measured in the blood of individuals having normal CYP2D6 enzymatic activity. For example, if the CYP2D6 enzymatic activity of a patient is estimated by one or more methods (e.g., genotyping, determination of dextromorphan blood levels) to be 50% of the enzymatic activity normally observed in an individual having normal CYP2D6 enzymatic activity, the dose for the patient may need to be adjusted to one-half of the dose given to an individual having normal CYP2D6 enzymatic activity. Similarly, for ultrarapid metabolizers, an analogous calculation will lead to the conclusion that a dose adjustment of twice that given an individual having normal CYP2D6 enzymatic activity may be needed in order to achieve similar blood levels for the parent compound and active metabolites.

Alternatively, the dose of iloperidone administered to a patient may be decreased based upon the patient's CYP2D6 genotype alone, or upon the patient's P88:P95 or (iloperidone+P88):P95 ratios. For example, if a patient has a "poor metabolizer" genotype, or has a high P88:P95 or (iloperidone+P88):P95 ratio, the patient's dose of iloperidone may be reduced by, for example, 25%, 50%, or 75%. A patient's genotype can be readily determined using standard techniques on samples of body fluids or tissue. Such techniques are disclosed, e.g., in PCT Application Publication Number WO03054226.

While the CYP2D6G1846A (AA or AG) genotype and the CYP2D6C100T (CT or TT) genotype are illustrated herein, the method of the invention can employ other genotypes that result in decreased activity of the CYP2D6 protein on iloperidone and P88. It is within the skill of the art, based on the disclosure herein, to identify additional CYP2D6 genotypes that result in decreased enzymatic activity on iloperidone and P88.

Furthermore, while the disclosure herein focuses on genotype, it is apparent to one of skill in the art that phenotype can also be used as an indicator of decreased activity of the CYP2D6 protein on iloperidone and P88. For example, McElroy et al. describe a correlation between CYP2D6 phenotype and genotyping as determined by dextromethorphan/ dextrorphan ratios. Therefore, although it is more convenient given the state of the art to look at genotype, if one were to determine that a given patient expressed a mutant CYP2D6 with lower activity on iloperidone and P88 than the wild type, or expressed abnormally low amounts of CYP2D6, then that patient would be given a lower dose of iloperidone than a patient with wild type CYP2D6, as discussed above. Alternative methods for determining the relative activity of a patient's CYP2D6 gene include biochemical assays to directly measure enzymatic activity, protein sequencing to examine the amino acid sequence of a patient's CYP2D6, monitoring transcription and translation levels, and sequencing the CYP2D6 gene mRNA transcript. For example, Chainuvati et al. describe assessment of the CYP2D6 phenotype using a multi-drug phenotyping cocktail (the Cooperstown 5+1 cocktail).

Iloperidone can be formulated into dosage units and administered to patients using techniques known in the art. See, e.g., PCT Application Publication Number WO03054226, US Patent Application Publication Number 20030091645, PCT Application Serial Number PCT EP03/ 07619, and PCT Application Publication Number WO02064141, all of which are incorporated herein by reference as though fully set forth.

In addition, the present invention provides a kit for determining a patient's CYP2D6 genotype and/or phenotype. Such a kit may include, for example, a detection means, a collection device, containers, and instructions, and may be used in determining a treatment strategy for a patient having one or more diseases or disorders for which iloperidone treatment is indicated.

Detection means may detect a CYP2D6 polymorphism directly or may detect the characteristic mRNA of the polymorphic gene or its polypeptide expression product. In addition, as will be recognized by one of skill in the art, detection means may also detect polymorphisms in linkage disequilibrium with a CYP2D6 polymorphism. Accordingly, any polymorphism in linkage disequilibrium with the CYP2D6 polymorphisms disclosed in this application may be used to indirectly detect such a CYP2D6 polymorphism, and is within the scope of the present invention.

Detection means suitable for use in the methods and devices of the present invention include those known in the art, such as polynucleotides used in amplification, sequencing, and single nucleotide polymorphism (SNP) detection techniques, Invader® assays (Third Wave Technologies, Inc.), Taqman® assays (Applied Biosystems, Inc.), gene chip assays (such as those available from Affymetrix, Inc. and Roche Diagnostics), pyrosequencing, fluorescence resonance energy transfer (FRET)-based cleavage assays, fluorescent polarization, denaturing high performance liquid chromatography (DHPLC), mass spectrometry, and polynucleotides having fluorescent or radiological tags used in amplification and sequencing.

A preferred embodiment of a kit of the present invention includes an Invader® assay, wherein a specific upstream "invader" oligonucleotide and a partially overlapping downstream probe together form a specific structure when bound to a complementary DNA sequence. This structure is recognized and cut at a specific site by the Cleavase enzyme, releasing the 5' flap of the probe oligonucleotide. This fragment then serves as the "invader" oligonucleotide with respect to synthetic secondary targets and secondary fluorescently-labeled signal probes contained in a reaction mixture. This results in the specific cleavage of the secondary signal probes by the Cleavase enzyme. Fluorescence signal is generated when this secondary probe, labeled with dye molecules capable of fluorescence resonance energy transfer, is cleaved. Cleavases have stringent requirements relative to the structure formed by the overlapping DNA sequences or flaps and can, therefore, be used to specifically detect single base pair mismatches immediately upstream of the cleavage site on the downstream DNA strand. See, e.g., Ryan et al., Molecular Diagnosis, 4; 2:135-144 (1999); Lyamichev et al., Nature Biotechnology, 17:292-296 (1999); and U.S. Pat. Nos. 5,846,717 and 6,001,567, both to Brow et al., all of which are hereby incorporated herein by reference.

Another preferred embodiment of a kit of the present invention includes a detection means comprising at least one CYP2D6 genotyping oligonucleotide specific to alleles known to predict a patient's metabolizer phenotype. More particularly, the means comprises an oligonucleotide specific for the CYP2D6G1846A or CYP2D6C100T polymorphism. The means may similarly comprise oligonucleotides specific for each polymorphism as well as the wild type sequence.

Detection methods, means, and kits suitable for use in the present invention are described in International Publication Nos. WO 03/0544266 and WO 03/038123, each of which is hereby incorporated herein by reference. It should also be understood that the methods of the present invention described herein generally may further comprise the use of a kit according to the present invention.

Collection devices suitable for use in the present invention include devices known in the art for collecting and/or storing a biological sample of an individual from which nucleic acids and/or polypeptides can be isolated. Such biological samples include, for example, whole blood, semen, saliva, tears, urine, fecal material, sweat, buccal smears, skin, hair, and biopsy samples of organs and muscle. Accordingly, suitable collection devices include, for example, specimen cups, swabs, glass slides, test tubes, lancets, and Vacutainer® tubes and kits.

The present invention encompasses treatment of a patient for any disease or condition that is ameliorated by administration of iloperidone. As discussed above, such diseases or conditions include, for example, schizoaffective disorders including schizophrenia, depression including bipolar depression, as well as other conditions such as cardiac arrythmias, Tourette's syndrome, psychotic disorders and delusional disorders.

A related aspect of the invention is a method for obtaining regulatory approval for a pharmaceutical composition comprising iloperidone or an active metabolite thereof, or a pharmaceutically acceptable salt of either, which comprises including in proposed prescribing information instructions to determine whether or not a patient is a CYP2D6 poor metabolizer prior to determining what dose to administer to the patient. In another related aspect, the invention is a method for commercializing (i.e., selling and promoting) pharmaceutical compositions comprising such compounds said method comprising obtaining regulatory approval of the composition by providing data to a regulatory agency demonstrating that the composition is effective in treating humans when administered in accordance with instructions to determine whether or not a patient is a CYP2D6 poor metabolizer prior to determining what dose to administer to the patient and then disseminating information concerning the use of such composition in such manner to prescribers (e.g., physicians) or patients or both.

Another aspect of the invention is a method for obtaining regulatory approval for the administration of iloperidone based, in part, on labeling that instructs the administration of a lower dose if the patient is already being administered a CYP2D6 inhibitor, e.g., paroxetine, etc.

While this invention has been described in conjunction with the specific embodiments outlined above, it is evident that many alternatives, modifications and variations will be apparent to those skilled in the art. Accordingly, the embodiments of the invention as set forth above are intended to be illustrative, not limiting. Various changes may be made without departing from the spirit and scope of the invention as defined in the following claims.

What is claimed is:

1. A method of decreasing a risk of QT prolongation in a patient being treated for schizophrenia with iloperidone, the method comprising:
   administering to the patient a dose of iloperidone that is 24 mg/day if, and because, the patient is not being treated with fluoxetine; and
   administering to the patient a dose of iloperidone that is 12 mg/day if, and because, the patient is being treated with fluoxetine.

* * * * *